(12) United States Patent
Jurik et al.

(10) Patent No.: US 6,531,322 B1
(45) Date of Patent: **\*Mar. 11, 2003**

(54) VISUAL BLOOD GLUCOSE TEST STRIP

(75) Inventors: Franklin A. Jurik, Pleasanton; Andrea Stubbs, Palo Alto; Mimi Diemmy Dao, San Jose; Carol Chang, San Francisco, all of CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/724,142

(22) Filed: Nov. 27, 2000

Related U.S. Application Data

(63) Continuation of application No. 09/133,857, filed on Aug. 13, 1998, now Pat. No. 6,162,397.

(51) Int. Cl.[7] .............................................. G01N 33/00
(52) U.S. Cl. ............................ 436/95; 422/58; 422/56; 436/170; 436/85
(58) Field of Search ............................. 422/56, 58, 57; 436/170, 95, 169

(56) References Cited

U.S. PATENT DOCUMENTS

| | | | | |
|---|---|---|---|---|
| 5,104,811 A | * | 4/1992 | Berger et al. ............... | 436/164 |
| 5,179,034 A | * | 1/1993 | Kiser et al. .................... | 435/14 |
| 5,200,325 A | * | 4/1993 | Blatt et al. ..................... | 435/14 |
| 5,306,623 A | * | 4/1994 | Kiser et al. .................... | 435/14 |
| 5,418,142 A | * | 5/1995 | Kiser et al. .................... | 435/14 |
| 5,563,031 A | * | 10/1996 | Yu ................................ | 435/14 |
| 5,719,034 A | * | 2/1998 | Kiser et al. .................... | 435/14 |
| 5,843,691 A | * | 12/1998 | Douglas et al. ................ | 435/14 |
| 5,962,215 A | * | 10/1999 | Douglas et al. ................ | 435/4 |
| 5,968,836 A | * | 10/1999 | Matzinger et al. ........... | 436/169 |

OTHER PUBLICATIONS

White–Stevens, Rodric H. et al., "Interference by Ascorbic Acid in Test Systems involving Peroxidase, II, Redox–Coupled Indicator Systems", Clinical Chemistry, vol. 28, No. 4, 1982, pp. 588–595.

Sherwood, Mark J. et al., "A New Reagent Strip (Vsidex–TM) for Determination of Glucose in Whole Blood", Clinical Chemistry, vol. 29, No. 3, 1983, pp. 438–446.

* cited by examiner

*Primary Examiner*—Jill Warden
*Assistant Examiner*—Samuel Siefke

(57) ABSTRACT

A visual blood glucose test strip has two membranes that each incorporate a reagent that reacts with glucose in a blood sample applied to the membranes to cause a color change. One of the membranes also includes an inhibitor and a dye. A blood sample applied to the strip causes the two membranes to form two different colors. Comparing the colors to a calibrated color chart permits a user to determine the glucose concentration in the blood sample.

1 Claim, 4 Drawing Sheets

VISUAL BLOOD GLUCOSE TEST STRIP

This is a continuation of U.S. patent application Ser. No. 09/133,857 filed Aug. 13, 1998, now U.S. Pat. No. 6,162, 397.

BACKGROUND OF THE INVENTION

1. Field of the Invention

This invention relates to a dry reagent strip that measures blood glucose concentration; more particularly, a strip that makes the glucose measurement without requiring a meter.

2. Description of the Related Art

Many visual test devices have been developed for measuring the concentration of certain analytes in biological fluids. These devices have, for example, measured glucose, cholesterol, proteins, ketones, phenylalanine, or enzymes in blood, urine, or saliva.

Among the devices that are in most widespread use today is the blood glucose monitor. In the U.S. alone, there are estimated to be more than 14 million people with diabetes. In order to avoid serious medical problems, such as vision loss, circulatory problems, kidney failure, etc., many of these people monitor their blood glucose on a regular basis and then take the steps necessary to maintain their glucose concentration in an acceptable range.

Reagent strips, that are used in these devices contain an indicator which turns a different shade of color, depending on the concentration of glucose in the whole blood sample that has been applied to the strip. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide.

U.S. Pat. No. 3,298,789, issued Jan. 17, 1967 to R. L. Mast, discloses a bibulous paper strip that incorporates a reagent composition which changes color when glucose-containing blood is applied to its surface. In use, the blood is wiped off one minute after being applied to the surface, and the color of the strip is compared with a color chart having color blocks representing specific glucose levels.

U.S. Pat. No. 3,630,957, issued Dec. 28, 1971 to H. Rey et al., discloses a plastic foil strip that is coated with a reagent composition. The process of use is similar to that disclosed in the earlier patent—apply blood, wait about a minute, compare the resultant color with a color chart.

U.S. Pat. No. 4,975,367, issued Dec. 4, 1990 to Albarella et al., discloses a color-match strip that is designed to provide different hues at different analyte concentrations, by using two independent indicator systems. It also discloses the option of including a color retardant to delay the catalytic effect of the independent systems, changing the final hue produced for a particular concentration of analyte.

U.S. Pat. No. 5,200,325, issued Apr. 6, 1993 to J. M. Blatt et al., discloses a "self-indicating" strip, in which color-chart comparisons are not required. The strip indicates whether an analyte is present at a predetermined concentration level by carrying out a subtractive reaction prior to the indicator reaction. Thereby the strip generates a predetermined response level only if the analyte is present at a predetermined concentration or more.

The patents discussed above involve "wipe-off" strips, in which the interference between the color of whole blood and the color developed by the indicator dye is minimized by wiping excess blood sample from the strip surface. Alternative approaches involve applying the blood sample to one surface of the strip and measuring the color on the opposite surface. The patents discussed below are examples.

U.S. Pat. No. 4,935,346, issued Jun. 19, 1990 to R. Phillips et al., discloses a meter, strip, and method for determining the glucose concentration in a sample of whole blood. The method involves simply applying a sample of whole blood to a first ("sample") surface of an inert porous matrix that is impregnated with a reagent. The sample migrates toward the opposite, "testing" surface, as the glucose interacts with the reagent to produce a light-absorbing reaction product. A reading of reflectance from the testing surface indicates the glucose concentration. Reflectance measurements are made at two separate wavelengths in order to eliminate interferences. A timing circuit is triggered by an initial decrease in reflectance caused by wetting of the testing surface by the sample having passed through the matrix.

U.S. Pat. No. 5,306,623, issued Apr. 26, 1994 to Kiser et al., discloses a visual blood glucose test strip that involves applying a glucose-containing whole blood sample to one side of the strip and taking the glucose reading on the opposite side, after red blood cells have been separated out and the sample has reacted with a reagent in the strip. An asymmetric polysulfone membrane was found especially useful as a single layer matrix for the strip. (See also U.S. Pat. No. 5,418,142, issued May 23, 1995 and U.S. Pat. No. 5,719,034, issued Feb. 17, 1998.)

U.S. Pat. No. 5,563,031, issued Oct. 8, 1996 to Y. S. Yu, discloses a dye couple useful in dry reagent strips for detecting analytes, such as glucose, in biological fluids. The dye couple comprises meta [3-methyl-2-benzothiazolinone hydrazone] N-sulfonyl benzenesulfonate monosodium combined with 8-anilino-1-naphthalene sulfonic acid ammonium (MBTHSB-ANS) and is used as an indicator in a reaction cascade producing a strong oxidizing agent, such as hydrogen peroxide. An advantage of the couple is that it is soluble in aqueous solution, but becomes insoluble upon oxidative coupling, thereby minimizing fading and providing a stable endpoint.

White-Stevens and Stover, *Clin. Chem.* 28, 589–595 (1982), discuss interference that can be caused by ascorbic acid on diagnostic tests. The ascorbic acid causes a lag time in color development of tests based on the use of peroxidase and redox indicators.

M. J. Sherwood et al., *Clin. Chem.* 29; 438–445 (1983) discuss a visual reagent strip for use in conjunction with a calibrated color scale. The strip uses two pads, each formulated for a different part of the normal range. The technology underlies the Visidex™ reagent strip, which is visually read. Other commercially-available visual strips include Dextrostix® reagent strips, Chem-strip bG®, and SinartStrip™ reagent strips.

SUMMARY OF THE INVENTION

In accordance with the present invention, a visual blood glucose test strip comprises a) a spreading layer for accepting a blood sample on a major surface and passing the sample to a second major surface, opposite;

b) an intermediate layer comprising first and second membranes, substantially side-by-side, each having a top major surface adjoining the second major surface of the spreading layer to receive a part of the blood sample and each containing a reagent that can react with glucose in the sample, as it passes through the membrane, to cause a color change in the reagent, the second membrane further comprising an inhibitor and a dye, and c) a support layer to support the other layers and to permit any color changes in the membranes to be visible through it.

As used in this specification and the appended claims, "reagent" refers to the components that may be on, or in, both membranes, as opposed to the inhibitor and dye, which are only on, or in, the second membrane. The dye is inert, in the sense that its color is substantially independent of the glucose concentration. Its purpose is to enhance the difference in color between the two membranes.

Among the advantages of the test strip of this invention are that it requires no wiping, can use a small blood sample, and provides results rapidly.

DETAILED DESCRIPTION OF THE INVENTION

Figure 1:
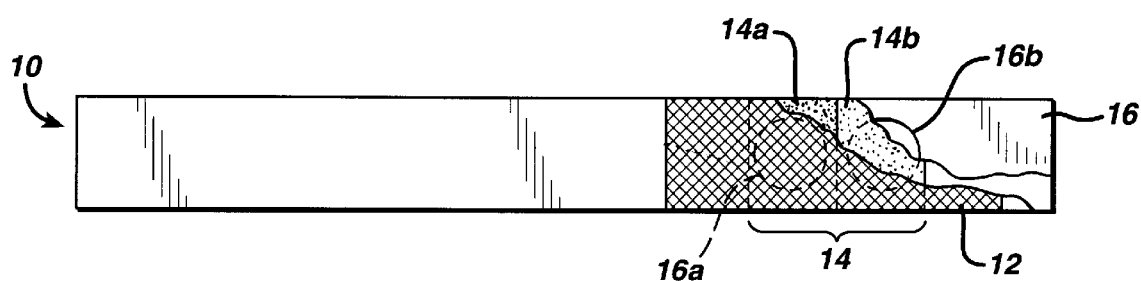
FIG. 1 is a top plan view of a test strip of this invention.
Figure 2:
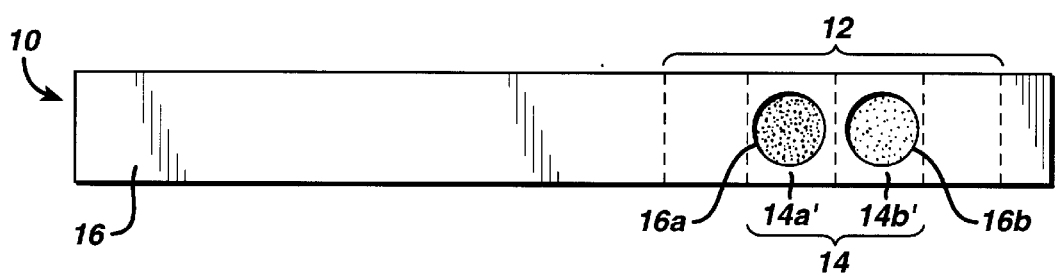
FIG. 2 is a bottom plan view of the test strip of FIG. 1.

This invention provides a no-wipe blood glucose strip that permits fast determination of blood glucose using a small sample of blood and without the need for a meter. FIG. 1 is a top plan view of the strip of the invention in partial cutaway, and FIG. 2 is a bottom plan view. As shown there, strip 10 has three components: a spreading top layer 12, an intermediate layer 14 that contains a reagent, and a support 16. Intermediate layer 14 consists of two side-by-side membranes 14a and 14b that are viewed through openings 16a and 16b, respectively, in support 16. Membrane 14a contains a reagent that reacts with glucose to cause a visible change in color. Membrane 14b contains a reagent that also reacts with glucose to cause a color change, but the color formed is different (as discussed below) from that formed in membrane 14a.

In operation a blood sample, which need be no larger than about 10 μL, is applied to spreading top layer 12. As the sample penetrates layer 12, it spreads out, so that sample is substantially uniformly distributed to membranes 14a and 14b. Glucose in the blood sample reacts with the reagents in the membranes as it passes toward support layer 16 to form colors. If support layer 16 is not transparent, the colors are viewed through optional openings 16a and 16b and compared with a calibration color chart to determine the blood glucose concentration.

A variety of materials are suitable for the spreading layer; for example, paper, glass fibers, polymer fibers, sintered plastics, woven and non-woven fabrics, and membranes. Preferred materials require minimum sample sizes, absorb the sample quickly, distribute it uniformly to the membranes, and do not interfere with the reagent chemistry in the membrane. Of course, cost is a practical consideration, as well. One preferred material for the spreading layer is a hydrophilic polyester woven mesh available from Tetko, Inc., Deprew, N.Y. Minimum sample size and rapid absorption suggest a thin layer. However good contact with the membranes is important, and that is difficult if the layer is so thin that it wrinkles easily. Commercially-available Tetko mesh 7-280/44 is among the thicker of the commercially-available meshes—255 micrometers—and does not easily wrinkle. Tetko mesh offers rapid absorption and low minimum sample size; however, it may not have the capacity to absorb a large blood sample, (undesirably) leaving excess sample on the surface of the spreading layer.

Another preferred spreading layer material is heat sintered plastic, such as polyethylene or polypropylene, that has been rendered hydrophilic by pre- or post-treatment with a blood compatible surfactant. One such material is a porous polyethylene treated with sodium methyl oleoyl taurate and available from the Porex Corp. of Fairburn, Ga. An advantage of this material is that it has unusually strong absorption, which causes fluid to be drawn away from the surface, where it might otherwise transfer to objects or people it contacts. The pores of this material range from about 20 micrometers to about 350 micrometers, preferably 50 to about 150 micrometers, or a mean of about 100 micrometers. Mesh that is about 0.5 to 0.6 mm thick, about 5 to 6 mm wide, and about 30 mm long is suitable.

Figure 3:
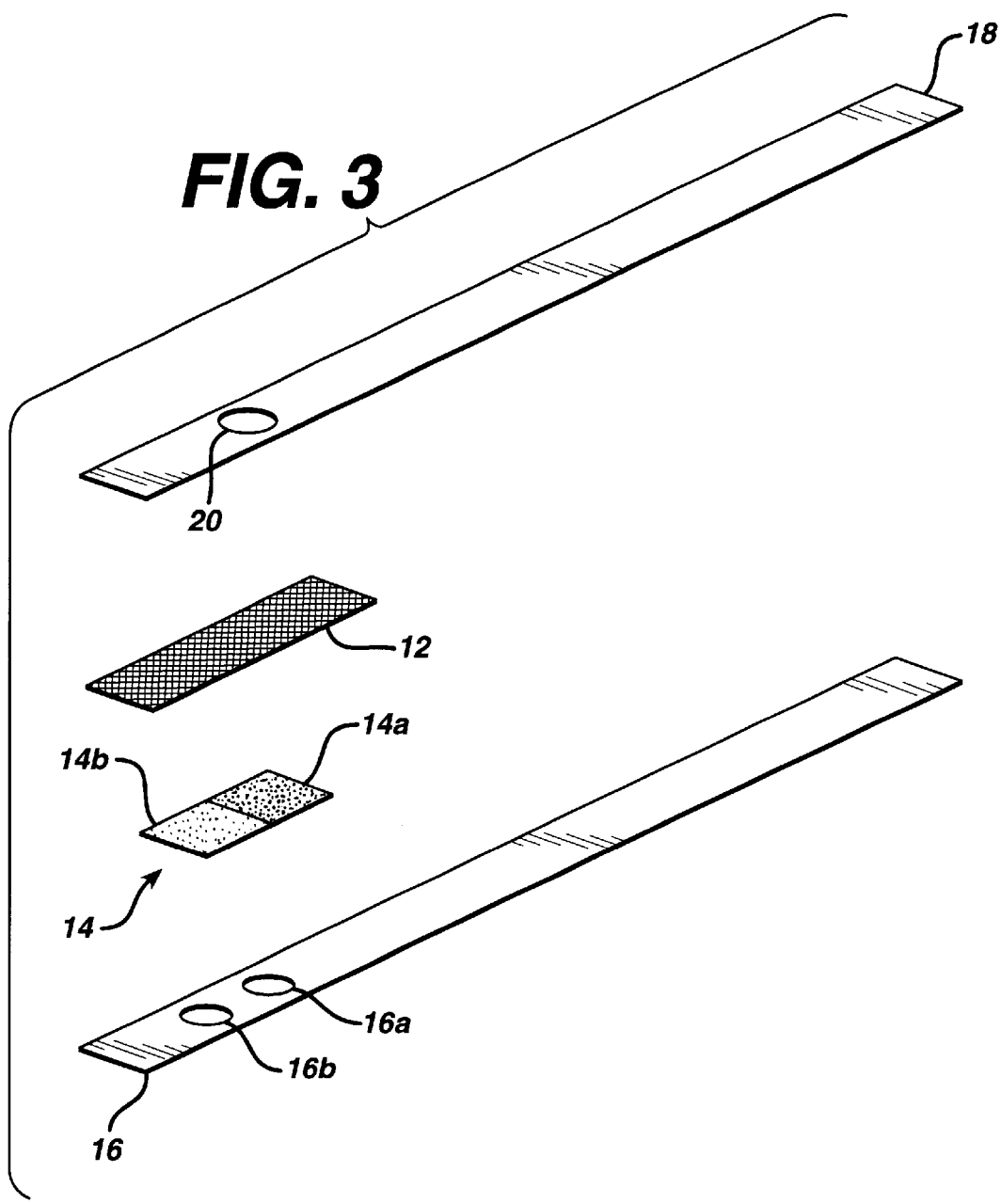
FIG. 3 is an exploded perspective view of another embodiment of a test strip of this invention.

FIG. 3 depicts an exploded view of a strip that permits larger sample size. The strip shown has, in addition to the elements shown in FIGS. 1 and 2, optional cover layer 18, with through hole 20 for applying sample to the spreading layer.

Figure 4:
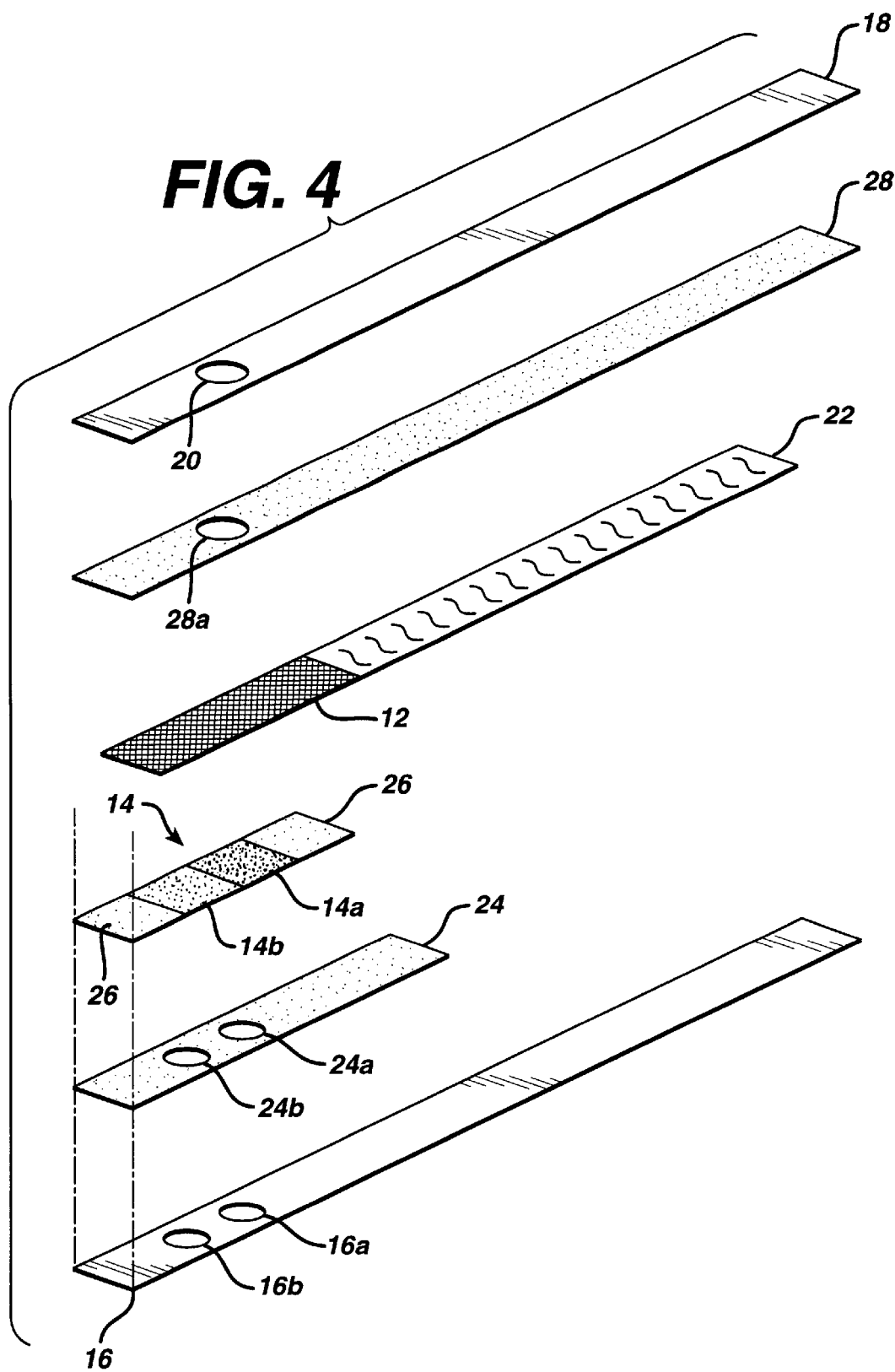
FIG. 4 is an exploded perspective view of yet another embodiment of a test strip of this invention.

FIG. 4 depicts an exploded view of another strip of this invention. In that embodiment, optional absorbent layer 22 adjoins spreading layer 12 for absorbing excess sample. When spreading layer 12 is of the thicker sintered polyethylene (Porex) type, absorbent layer 22 is generally not necessary. However, when the spreading layer is of the woven mesh (Tetko) type, which has lower fluid-holding capacity, absorbent layer 22 is preferably present.

Optionally, the elements of the strip are bonded together with an adhesive, and double-sided adhesive tape is a convenient adhesive to use. The embodiment of FIG. 4 includes adhesive layer 24 (with through openings 24a and 24b) for joining support layer 16 to intermediate layer 14; adhesive layers 26 for joining intermediate layer 14 to spreading layer 12; and adhesive layer 28 (with through opening 28a) for joining cover layer 18 to spreading layer 12 and absorbent layer 22. Adhesive layers 26 are shown abutting membranes 14a and 14b; however, the relative placement is not critical. Thus there can be a gap between the membrane and adhesive layer or they can overlap slightly.

Membrane materials and reagents most suitable for use in the strips of this invention provide fast reaction times, use minimum sample sizes, and yield uniform color, with stable endpoints. In addition, the blood color should be substantially hidden from the viewing side, so that it doesn't interfere with the evaluation. Based on these criteria, the preferred membrane material is an asymmetric polysulfone membrane whose pore size gradually increases from one surface to the opposite surface. (See U.S. Pat. No. 4,629,563, issued Dec. 16, 1986, to Wrasidlo.) This type of membrane is available from the Memtec Div. of U.S. Filter Co., San Diego, Calif. These membranes provided uniform color development and stable endpoints with samples of 10 μL or less in less than 45 seconds. The ability of the membranes to hide the blood color from the viewing side depends on their pore size. Large pores don't hide the blood color well, but membranes with pores smaller than about 0.10 μm have a tendency to crack after being coated with reagent. The pore size designated for an asymmetric membrane is the size of the smaller pores. Preferably, membranes with pore sizes less than about 1.0 μm, more preferably about 0.15 to 0.35 μm are used and give acceptable blood hiding in the hematocrit range 30–55%. Such membranes include Memtec membranes BTS 30, 45, 55, and 65. Preferably, both membranes 14a and 14b are of the same material. About 10 μL of blood are typically required to saturate both test pads, but excess blood is absorbed up to a volume determined by the porosity and dimensions of the spreading layer material.

The reagent composition incorporated into both membranes reacts with glucose in the blood sample to cause a detectable color change. Among suitable compositions are those disclosed in the above-mentioned U.S. Pat. Nos. 4,935,346 and 5,563,031, and those patents are incorporated herein by reference. Generally, these compositions comprise a component for converting glucose to hydrogen peroxide, such as glucose oxidase, and one or more components for detecting the hydrogen peroxide produced from the glucose present in the sample. The components for detecting hydrogen peroxide may be a peroxidase, preferably horseradish peroxidase, together with an "indicator" that changes color in the course of the reaction. The indicator may be an oxidizable dye or a dye couple. The peroxidase catalyzes the oxidation of the indicator in the presence of hydrogen peroxide. The indicator may be 3-methyl-2-benzothiazolinone hydrazone hydrochloride combined with either 3,3-dimethylaminobenzoic acid (MBTH-DMAB) or 8-anilino-1-naphthalene sulfonic acid ammonium (MBTH-ANS). Alternatively, the indicator may be meta [3-methyl-2-benzothiazolinone hydrazone] N-sulfonyl benzenesulfonate monosodium combined with 8-anilino-1-naphthalene sulfonic acid ammonium (MBTHSB-ANS). The latter combination is preferred.

Membrane 14b also includes an inhibitor, to delay the color-forming reaction, and a dye. Membrane 14a, with the color-forming reagent composition alone, permits several levels in the low-glucose range to be distinguished; e.g., 25, 50, and 80 mg/dL. For higher glucose concentration, the color is too dark to permit reliable discrimination among glucose levels. Color development in membrane 14b is inhibited, so that, depending on the inhibitor concentration used, color development can start at higher glucose levels. A number of different inhibitors are suitable, including 2,3,4-trihydroxybenzoic acid, propyl gallate, and ascorbic acid (see the above-mentioned U.S. Pat. No. 5,306,623). Ascorbic acid is preferred, and preferably the ascorbic acid concentration is selected to delay color development until glucose levels reach about 120 mg/dL.

Including an inert dye with the inhibitor produces a different color to provide even better glucose level discrimination. Among suitable inert dyes are mordant yellow, primulin direct yellow, primaquine diphosphate, thiazole yellow G, brilliant yellow, and auramine O-anhydrous. By varying dye type and concentration, various hues of green, yellow, purple, or blue can result. Auramine O-anhydrous at 0.1% concentration is preferred, because in combinatio with MBTHSB-ANS it gives a bright green color, maximum visual resolution between glucose levels, and excellent coating uniformity. In combination, the preferred reagent compositions in membranes 14a and 14b permit a user to discriminate among eight levels of glucose concentration in the range from 25 to 600 mg/dL.

To further enhance the blood-hiding effect, and thereby permit measurements over a broader range of sample hematocrit, various water-soluble charged polymers may be added to the reagent, including polyvinylpyrrolidone (PVP), GAFQUAT*, polyacrylic acid, and polystyrene sulfonic acid. Empirically, PVP is preferred.

The following examples demonstrate the present invention in its various embodiments, but are not intended to be in any way limiting.

EXAMPLE 1

A reagent strip was prepared using hydrophilic asymmetric polysulfone membrane having a pore size of 0.2 μm (Memtec BTS-55). The membrane was coated by allowing the dull side (larger pore size) to contact Solution 1 (kiss-coating). Excess solution was removed by wiping the membrane strip with a glass rod. The membrane was air dried in a forced air oven at 56° C. for 10 minutes.

| The composition of the coating was: SOLUTION 1 | |
|---|---|
| Water | 25 mL |
| Citric acid | 0.282 g |
| Trisodium citrate | 0.348 g |
| Manitol | 0.25 g |
| EDTA | 0.021 g |
| Gantrez | 0.1125 g |
| Crotein | 0.36 g |
| Glucose Oxidase | 0.36 g (125 Units/mg) |
| Horseradish peroxide | 0.071 g (501 Units/mg) |
| Carbopol Solution* | 1.25 mL |
| *(0.1375 g in 1.25 mL of MeCN) | |
| Citrate Buffer* | 3.75 mL |
| *(0.13 g disodium citrate in 5.0 mL water) | |

For the low range membrane (14a), a Solution 1-coated membrane was then kiss-coated with dye Solution 2 and dried in the same oven as above for 5 minutes.

| The dye solution 2 composition was: SOLUTION 2 | |
|---|---|
| Solvent* | 38.16 mL |
| MBTHSB | 0.1552 g |
| ANS | 0.2142 g |
| 20% Maphos (solvent) | 1.84 g |

(*solvent: 50% water, 30% EtOH, and 20% MeOH)

For the high range membrane (14b), the membrane coated with Solution 1 was then kiss-coated with dye Solution 3 and dried in the same oven as above for 5 minutes.

| The dye solution composition was: SOLUTION 3 | |
|---|---|
| Solvent* | 38.16 mL |
| MBTHSB | 0.1552 g |
| ANS | 0.2142 g |
| 20% Maphos (solvent) | 1.84 g |
| Auramine O | 0.0316 g |
| Ascorbic Acid | 0.13 g |

(*solvent: 50% water, 30% EtOH, and 20% MeOH)

The resulting membranes were cut into strips 0.6 cm wide and used to make the strips depicted in FIGS. 1 and 2.

Figure 5:
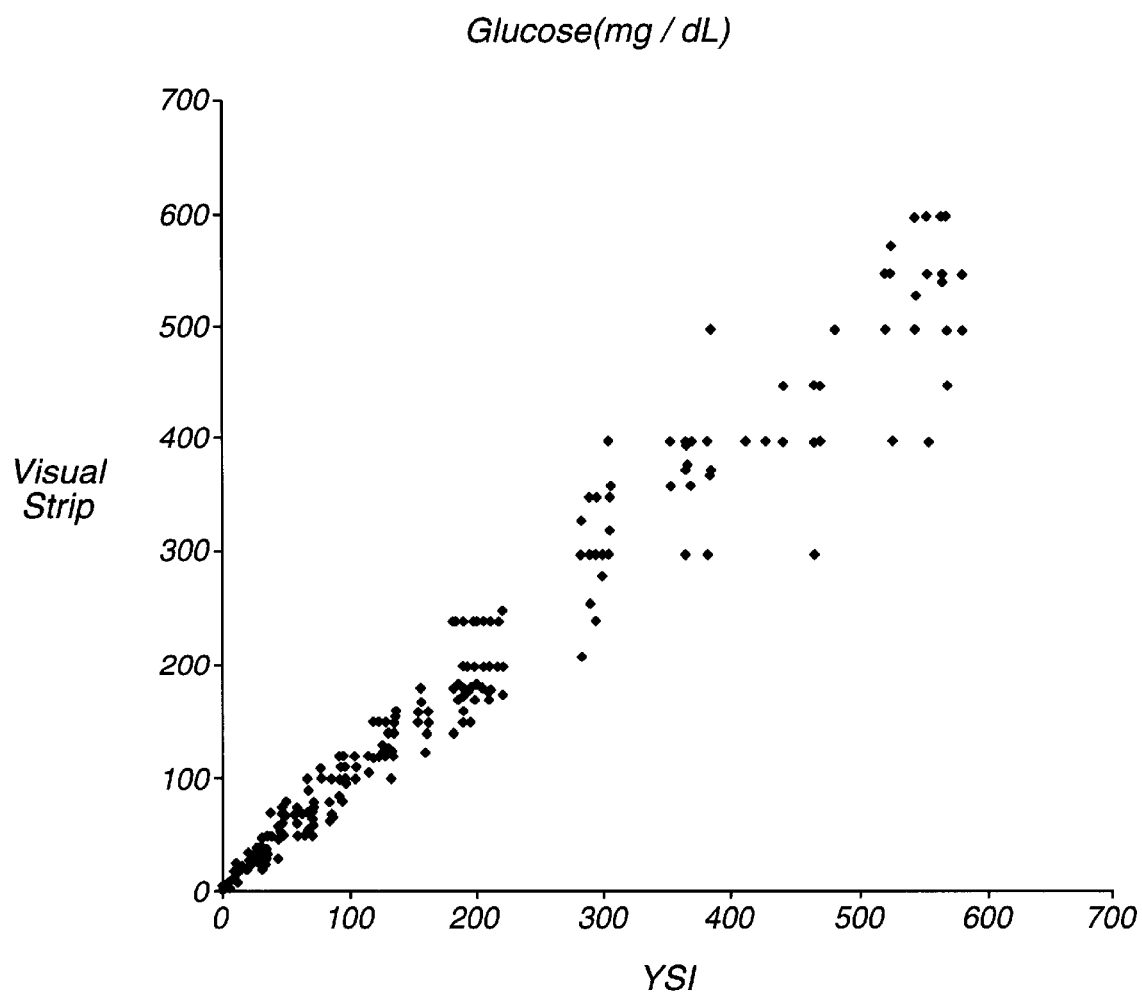
FIG. 5 is a scattergram of glucose values as measured by an embodiment of the present invention plotted against values measured on a standard meter.

The strips were tested by visual comparison with a color chart (Table 1) that was constructed of Munsell color chips and calibrated to the range of glucose values from 0–600 mg/dL. The random testing of 288 spiked venous blood samples gave excellent correlation ($R^2=0.965$) to the determinations made on a standard blood glucose meter—Yellow Springs Instruments (YSI) Model 2300 STAT Glucose Analyzer -corrected for plasma glucose values (FIG. 5).

EXAMPLE 2

The procedure of Example 1 was followed, except that Solutions 1 and 2 (or 3) were coated onto the small-pore side of the membrane and a coating of a blood-hiding polymer was added over the coating of dye solution. A number of different polymers were tested. Aqueous solutions of each of the following were effective in hiding the blood color:

Polyvinyprypolidone—MW 160,000, 2%

GAFQUAT 734 (copolymer of quaternized vinylpyrrolidone and dimethylaminoethyl methacrylate)—MW 60,000–100,000, 7%

Sodium salt of polystyrene sulfonic acid—MW 70,000, 7%

TABLE 1

Munsell Notation* for Color Chart

| Glucose levels (mg/dL) | Pad #1 | | | Pad #2 | | |
|---|---|---|---|---|---|---|
| 0 | 10 | P | 7/2 | 10 | YR | 7/6 |
| 25 | 5 | PB | 6/2 | 2.5 | Y | 6/8 |
| 50 | 10 | B | 6/4 | 2.5 | Y | 6/8 |
| 80 | 10 | B | 5/4 | 2.5 | Y | 6/8 |
| 120 | 2.5 | PB | 5/6 | 7.5 | Y | 6/6 |
| 180 | 2.5 | PB | 4/8 | 5 | GY | 5/6 |
| 240 | 5 | PB | 4/8 | 10 | GY | 5/6 |

TABLE 1-continued

Munsell Notation* for Color Chart

| Glucose levels (mg/dL) | Pad #1 | | | Pad #2 | | |
|---|---|---|---|---|---|---|
| 400 | 7.5 | PB | 3/10 | 5 | G | 4/6 |
| 600 | 5 | PB | 3/8 | 10 | G | 3/4 |

*see The Munsell Book of Color, Macbeth div. Of Kollmorgen Instruments Corp., New Windsor, NY

What is claimed is:

1. A method for measuring a concentration of glucose in a sample of whole blood, comprising the steps of
   a) providing a test strip that comprises
      (i) a two-sided spreading layer for accepting the blood sample on a first side and passing the sample to a second side, opposite:
      (ii) an intermediate layer comprising first and second membranes, substantially side-by-side, each having a top major surface adjoining the second side of the spreading layer to receive a part of the blood sample and each containing a reagent that can react with glucose in the sample, as it passes through the membrane, to cause a color change in the reagent, the second membrane further comprising an inhibitor and an inert dye, and
      (iii) a support layer to support the other layers and to permit any color changes in the membranes to be visible through it
   b) applying the blood sample to the spreading layer of the test strip, and
   c) determining the glucose concentration by comparing the colors of the first and second membranes with a calibration color chart.

* * * * *